United States Patent [19]

Saunal et al.

[11] Patent Number: 6,010,716
[45] Date of Patent: Jan. 4, 2000

[54] PHARMACEUTICAL COMPOSITION FOR TRANSDERMAL ADMINISTRATION

[75] Inventors: Henry Saunal; Brigitte Illel, both of Montpellier, France

[73] Assignee: Sanofi, Paris, France

[21] Appl. No.: 08/930,004

[22] PCT Filed: Mar. 29, 1996

[86] PCT No.: PCT/FR96/00480

§ 371 Date: Dec. 3, 1997

§ 102(e) Date: Dec. 3, 1997

[87] PCT Pub. No.: WO96/30000

PCT Pub. Date: Oct. 3, 1996

[30] Foreign Application Priority Data

Mar. 30, 1995 [FR] France ............................... 95 03776

[51] Int. Cl.[7] ............................. A61L 15/28; A61L 25/00; A61M 37/00
[52] U.S. Cl. ........................ 424/449; 602/904; 514/947; 604/304
[58] Field of Search ............................ 424/487, 488, 424/443, 447–449; 602/39, 904; 514/947; 604/304

[56] References Cited

U.S. PATENT DOCUMENTS 4,842,864 6/1989 Guillemet et al. .

FOREIGN PATENT DOCUMENTS

| 0 055 396 | 7/1982 | European Pat. Off. . |
| 0 055 397 | 7/1982 | European Pat. Off. . |
| 0 289 900 | 11/1988 | European Pat. Off. . |
| 0 319 964 | 6/1989 | European Pat. Off. . |
| 0 640 352 | 3/1995 | European Pat. Off. . |
| 88 09185 | 12/1988 | WIPO . |
| 94 13257 | 6/1994 | WIPO . |
| 95 09195 | 4/1995 | WIPO . |

*Primary Examiner*—Edward J. Webman
*Attorney, Agent, or Firm*—Jacobson, Price, Holman & Stern, PLLC

[57] ABSTRACT

The invention concerns a pharmaceutical composition for transdermal administration, characterized in that it comprises:

a) optionally, a polymeric release matrix capable of forming a flexible film after drying, chosen from cellulose polymers or copolymers or vinylpyrrolidone/vinyl acetate copolymers b) an active principle c) a promoter of transcutaneous absorption of the active principle d) a physiologically acceptable non-aqueous solvent capable of dissolving the release matrix, the active principle and the transcutaneous absorption promoter and also capable of being rapidly removed by evaporation on contact with the skin.

35 Claims, No Drawings

PHARMACEUTICAL COMPOSITION FOR TRANSDERMAL ADMINISTRATION

The present invention relates generally to a novel pharmaceutical composition for transdermal administration.

More precisely, the invention relates to a pharmaceutical composition for transdermal administration, which is capable of forming a flexible film after drying on the skin, as well as to a matrix which may be used in such a pharmaceutical composition.

The transdermal administration of medicinal active principles represents a persuasive technique since it is non-invasive and is endowed with certain advantages such as the absence of gastrointestinal side effects or of degradation of the active substance by liver enzymes.

To be more effective, this technique should, however, allow transcutaneous penetration of the medicinal product over a prolonged period and in a manner which is sufficient to reach plasma levels compatible with a therapeutic treatment.

Oestradiol, along with other hormones, is a substance which is resorbable through the skin by means of an adapted formulation.

Since low doses, from about 50 to 120 pg/ml of plasma, are necessary for clinical effectiveness, for example for the treatment of oestrogen deficiencies, oestradiol represents an active principle of choice for transdermal application.

To date, various systems or devices for this type of administration have been proposed, these making it possible to introduce controlled doses of medicinal substances in general and oestradiol in particular into the blood flow.

For example, the transdermal administration device known commonly as a "patch" is known, this device consisting of a reservoir formed of synthetic plastic materials containing the active principle. This reservoir may be covered, on its face in contact with the skin, with a microporous membrane whose permeability to the active substance regulates its diffusion and consequently its dosage.

Despite the real possibilities offered by this device, in particular for application to oestradiol, other systems may be preferred over it. The reason for this is that it is known that the patch may become detached from the skin and, moreover, may often have an unaesthetic appearance.

Gels containing oestradiol have also been proposed. However, this pharmaceutical form may have certain drawbacks during use, generally a sticky feel which the patient finds unpleasant, as well as difficulty in governing the dose of active principle administered and delicate control of the surface to be covered.

Other systems which aid the transdermal administration of medicinal principles have also been reported.

In this respect, mention may be made of sprayable compositions containing, in particular, polymers capable of forming a film on contact with the skin and of releasing the active principle for transcutaneous administration. Compositions of this type, described for example in patent EP 0,319,555, comprise an active principle, a polymer matrix forming a flexible film after drying, a solvent controlling the release of the active substance, namely a macrogollaurate sorbitan, a paraffin, a fatty acid diglyceride or triglyceride of average chain length or propylene carbonate, as well as a solvent, for the matrix, capable of evaporating on the skin and, lastly, a propellant making it possible to spray this composition contained in a suitable device.

A matrix consisting of ethylcellulose is, however, not recommended for use therein on account of its tendency to block the spraying system.

In the context of the present invention, a sprayable composition, according to the EP patent mentioned above, containing 2% oestradiol as active principle has been tested.

However, after tests performed on naked rat skin, an oestradiol flow of only about 0.03 $\mu$g $h^{-1}$ $cm^{-2}$ at equilibrium was recorded, which would lead one to expect fairly limited performance levels and efficacy when the situation is one of applying these compositions to a reduced area of skin for the purpose of a therapeutic treatment.

Moreover, compositions such as those proposed by the above mentioned patent, characterized by the presence of a propellant gas, for example a halogenated hydrocarbon, are increasingly surrounded with controversy following the potential risks that they are liable to have on the environment.

In addition, on account of the presence of polymethacrylic derivatives, the compositions of patent EP 0,319,555 release a characteristic odour which is quite unpleasant for the patient and those in his immediate vicinity.

Other pharmaceutical compositions for topical administration containing an active principle, a solvent and various other ingredients are also known.

By way of example, mention may be made of patent EP 55,396, which describes antimycotic compositions formed:

of a cellulose ether of 2 to 10% of a spreading agent such as isopropyl myristate or isopropyl palmitate of 1 to 8% of a solubilizing agent of 0.05 to 1% of an active principle and of a solvent such as isopropanol.

However, although they may be used for dermatological topical applications, these compositions prove to be totally unsuitable for an application by spraying, even after addition of 10 to 40% of a propellant gas as recommended, since they appear to be too viscous and liable to entrain various drawbacks such as blocking of the spraying device.

Patent EP 319,964 may also be mentioned, this patent describing antifungal compositions capable of forming a film comprising:

from 0.1 to 1.5% of tolnaphthalate from 10 to 20% of a dimethylaminoethyl methacrylate/methacrylate copolymer from 0.5 to 10% of a fatty acid ester a solvent of alcohol type and optionally from 0.1 to 5% of a cellulose derivative.

This composition does not appear to be suitable for spraying either. Moreover, as already mentioned above, the presence of methacrylic derivatives gives it an off putting odour.

Lastly, patent EP 289,900 may be mentioned, which relates to antibacterial compositions for topical use comprising:

from 0.5 to 10% of an antibacterial active principle from 1 to 30% of a water-insoluble polymer, in particular ethylcellulose or a polyvinylpyrrolidone copolymer from 0.5 to 40% of a plasticizer, generally an essential oil, which also acts as transcutaneous absorption promoter from 50 to 95% of a solvent such as ethanol.

As is known, the essential oils consist in larger majority of terpene derivatives.

In the context of the invention, a composition similar to that described in this patent was investigated, this composition containing, in particular, oestradiol as active principle and limonene, which is a terpene, as transdermal absorption promoter. However, such a composition gave only very weak transcutaneous diffusion flows of this active principle.

The search for a composition which allows the transdermal diffusion of medicinal active principles, in particular oestradiol, from a weak coating surface and at levels compatible with a therapeutic treatment while at the same time being free of the drawbacks reported above remains of major interest.

Now, it has surprisingly been found, according to the invention, that it is possible to provide pharmaceutical compositions for the transdermal administration of oestradiol, or of other medicinal substances, from a film formed on the skin, these compositions being free of the drawbacks mentioned above but capable, from a reduced and controllable area of coverage, of delivering the active principle into the bloodstream in a uniform and continuous manner and at plasma levels largely reaching the therapeutic thresholds.

Thus, the main subject of the invention is a pharmaceutical composition for transdermal administration comprising:
1) optionally, a polymeric release matrix capable of forming a flexible film after drying
2) an active principle
3) a promoter of transcutaneous absorption of the active principle
4) a physiologically acceptable non-aqueous solvent capable of dissolving the release matrix, the active principle and the transcutaneous absorption promoter and also capable of being rapidly removed by evaporation on contact with the skin.

In the present context, both in the description and in the claims, the term "active principle" refers either to a medicinal substance intended, after administration, to bring about a preventive or therapeutic response, or to a combination of two or more substances of this type.

The polymeric matrix is generally chosen from polymeric or copolymeric substances capable both of forming a flexible film after evaporation of the solvent and of releasing the active principle.

Generally, this matrix is present in a proportion of from 0% to 6% of the weight of the composition according to the invention, for example from 4% to 6%, for example 5%. Preferably, from 1 to 5% by weight of matrix is used, in particular 5%.

The choice of this matrix focuses mainly on polymeric or copolymeric substances which are soluble in the physiological solvent so as to form a homogeneous solution.

Among the polymers or copolymers capable of satisfying the above criteria, cellulose polymers or copolymers are more particularly selected, in particular because they have, after drying, suitable resistance to abrasion and mechanical stability. For this reason, cellulose matrices of this type may be rinsed with water without fear of deterioration or alternatively of elimination of the active principle.

As examples of such cellulose polymers or copolymers which can be used in the compositions of the invention, mention may be made of ethylcellulose, cellulose acetate butyrate, cellulose acetate propionate or a grafted or ungrafted hydroxypropylmethylcellulose, such as hydroxypropylmethylcellulose acetate succinate.

However, ethylcellulose represents the preferred cellulose polymer and, consequently, the polymeric release matrix of choice for the formation of a flexible film on contact with the skin.

Moreover, the polymeric matrix may consist of a vinylpyrrolidone/vinyl acetate copolymer such as polyvinylpyrrolidone/vinyl acetate, referred to hereinbelow as PVP VA.

Consequently, according to another aspect thereof, the subject of the invention is a pharmaceutical composition for transdermal administration comprising:
1) a polymeric release matrix capable of forming a flexible film after drying, chosen from cellulose polymers or copolymers or from vinylpyrrolidone/vinyl acetate copolymers
2) an active principle, in particular oestradiol
3) a promoter of transcutaneous absorption of the active principle
4) a physiologically acceptable non-aqueous solvent capable of dissolving the release matrix, the active principle and the transcutaneous absorption promoter and also capable of being rapidly removed by evaporation on contact with the skin.

As regards the active principle, it will be chosen from medicinal substances which are soluble in the physiologically acceptable solvent and which are capable of crossing the epidermis and the dermis in a continuous manner, at a flow which is sufficient to give a therapeutically effective blood concentration from a skin area of reduced but sufficient size.

Such substances will be selected from active principles which show a relatively short biological half-life and a sizeable physiological effect at low plasma levels.

Besides oestradiol, which constitutes a preferred active principle according to the invention, mention may be made of various medicinal substances which may be incorporated advantageously into compositions according to the invention. These substances may be chosen from the following groups:

a bronchodilator such as sodium cromoglycate salbutamol or theophylline a diuretic agent such as furosemide or hydrochlorothiazide an antibacterial agent such as a penicillin, a cephalosporine, tetracycline, oxytetracycline, chlortetracycline or chloramphenicol an antiacne agent such as erythromycin a sedative or tranquillizer such as pentobarbital or the sodium salt thereof, secobarbital or the sodium salt thereof, or codeine a psychostimulant such as 3-(2-aminopropyl)indole acetate or 3-(2-aminobutyl)indole acetate an anxiolytic agent such as diazepam, chlordiazepoxide, reserpine, chlorpromazine or thiopropazate a hormone such as an adrenocorticosteroid, for example 6-methylprednisolone an androgenic steroid, for example testosterone or methyltestosterone an oestrogenic steroid, for example oestrone or ethynylestradiol a progestative steroid, for example progesterone, 17-α-hydroxyprogesterone, medroxyprogesterone or the acetate thereof, 19-norprogesterone, norethindrone, norethindrone acetate, demegestrone or nomegestrol acetate a thyroid hormone such as thyroxine an antipyretic agent such as acetylsalicylic acid, salicylamide, sodium salicylate or methyl salicylate a narcotic analgesic such as morphine or a major analgesic a hypoglycaemiant, for example a sulphonylurea such as glypizide, glyburic, chlorpropamide or insulin an antispasmodic agent such as atropine or methscopolamine bromide an antitabagic agent such as lobeline or nicotine an antimalaria agent such as 4-aminoquinoline or 9-aminoquinoline a beta-blocker such as metoprolol an antiarthritic agent such as sulindac a non-steroidal anti-inflammatory agent such as ibuprofen or naproxene an anti-osteoporotic agent such as etidronate, tiludronate or the sodium salts thereof a skin bleaching agent such as ascorbic acid a vasodilator such as dipyridamole, trinitrine or isosorbide dinitrate an anti-hypertensive agent such as propanolol, prazosin, diltiazem or clonidine an antiparkinsonian agent such as methyldopa or selegiline an antimigraine agent such as dihydroergotamine an antiulcer agent such as cimetidine an anticancer agent such as tamoxifen a nutritional supply such as vitamins, essential amino acids or essential fatty acids.

These medicinal active principles, comprising oestradiol, will be incorporated into the compositions of the invention in a proportion in particular of from 0.1% to 20% of the weight of these compositions, it being understood that each active principle will be introduced at individualized concentrations known in the state of the art for transdermal administration or concentrations adapted to this route of administration.

For example, the oestradiol may be present among the compositions of the invention in a proportion of from 0.5% to 6% of the weight of this composition, in particular from 0.5% to 4%, preferably from 1% to 2%.

As mentioned above, the compositions of the invention may optionally contain an active principle formed of a combination of several medicinal substances selected from the groups listed above.

Examples which may be mentioned are an oestroprogestative combination for the treatment of menopausal symptoms, consisting of an oestrogenic steroid such as oestradiol or a progestative steroid such as norethindrone acetate, or alternatively a contraceptive combination such as levonorgestrel/oestradiol.

So as to reach an effective blood concentration of active principle without, however, covering too large an area of skin, the polymeric matrix and the active principle are combined with a transcutaneous absorption promoter. This promoter enters into the compositions of the invention advantageously in a proportion of from 15% to 30% of the weight of this composition, preferably from 15% to 25%, for example 20%.

This absorption promoter is chosen such that it can bring about sizeable transdermal flows in order to reach the desired plasma concentrations by means of an acceptable level of skin coverage, that is to say less than 150 cm$^2$ but preferably between 10 and 40 cm$^2$, for example 30 cm$^2$.

In order to be effective, the transcutaneous absorption promoter in question must be capable of temporarily disrupting the skin barrier so as to increase the permeability of the skin without irritating it, while at the same time promoting the diffusion of the chosen active principle according to kinetics and a concentration which are sufficient and which may be maintained for a certain period.

This transcutaneous absorption promoter will be selected from substances which are soluble in the non-aqueous physiological solvent capable of evaporating rapidly on contact with the skin.

It will preferably be selected from the following compounds, which have the necessary degree of solubility in the physiological solvent in question and which unite the best qualities reported above, that is to say from:

aliphatic fatty acid esters, essentially esters having from 10 to 30 carbon atoms in total optionally substituted with one or two hydroxyl, carboxylic or $C_1$–$C_4$ acyloxy groups such as acetoxy, or optionally interrupted by one or two ethylenic bonds or by one or two ether oxygens aliphatic fatty alcohols, essentially $C_{10}$–$C_{30}$ alcohols optionally substituted with one or two hydroxyl, carboxylic or $C_1$–$C_4$ acyloxy groups, such as acetoxy, or optionally interrupted by one or two ethylenic bonds or by one or two ether oxygens.

Particularly preferred absorption promoters which may be selected from aliphatic fatty acid esters and aliphatic fatty alcohols mentioned above are reported below, namely:

a) aliphatic fatty acid esters of general formula:

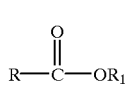

I in which R represents a linear or branched $C_2$–$C_{17}$ alkyl or alkenyl group optionally substituted with a hydroxyl, carboxylic or $C_1$–$C_4$ acyloxy group and $R_1$ represents a linear or branched $C_3$–$C_8$ alkyl group optionally substituted with one or two hydroxyl groups such as, for example, an isopropyl, 2-ethylhexyl or 1,2-dihydroxyethyl group, or $R_1$ represents a group —$CH_2$—$CH_2$—O—$(CH_2)_2$—O—$CH_2$–$CH_3$, the aliphatic fatty acid ester containing a minimum of 10 carbon atoms and a maximum of 2 hydroxyl groups b) aliphatic fatty alcohols of general formula:

II in which $R_2$ represents a $C_{10}$–$C_{20}$ alkyl group.

With respect to specific compounds which have shown the best potential to promote the transcutaneous absorption of active principles, in particular oestradiol, mention may be made of:

2-ethylhexyl 2-ethylhexanoate (Compound 1)

isopropyl myristate (Compound 2)

diethylene glycol monoethyl ether myristate (Compound 3)

isopropyl palmitate (Compound 4)

2-octyldodecanol (Compound 5)

2-ethylhexyl undecylenate (Compound 6)

2-ethylhexyl succinate (Compound 7)

2-ethylhexyl 12-hydroxystearate (Compound 8)

2-ethylhexyl 12-acetoxystearate (Compound 9) glyceryl isostearate (Compound 10) hexyl laurate (Compound 11).

2-Ethylhexyl 2-ethylhexanoate represents the preferred absorption promoter, in particular for transdermal compositions according to the invention whose active principle is oestradiol.

As regards the physiologically acceptable non-aqueous solvent capable of dissolving the release matrix, the active principle and the transcutaneous absorption promoter, it is selected from compounds with a relatively low boiling point, namely below 100° C. at atmospheric pressure, such that it can be eliminated rapidly by evaporation on contact with the skin and such that it can assist, in the same manner, in the formation of a film by drying without, however, giving rise to local irritation.

Such physiologically acceptable solvents are generally used in a proportion of from 44% to 84.9% of the weight of the final composition and may be selected from volatile compounds such as dichloromethane, ethanol, isopropanol or ethylacetate.

Ethanol and isopropanol constitute solvents of choice. However, ethanol represents a preferred solvent according to the invention since it contributes efficiently towards the formation of particularly homogeneous films while at the same time evaporating rapidly on contact with the skin.

Consequently, according to one of the specific aspects thereof, the invention relates to a transdermal composition comprising:

1) from 0% to 6% of a polymeric release matrix capable of forming a flexible film after drying, chosen in particular from cellulose polymers or copolymers such as ethylcellulose
2) from 0.1% to 20% of an active principle, in particular from 1% to 2% of oestradiol
3) from 15% to 30% of a promoter of transcutaneous absorption of the active principle, in particular from 15% to 25% of a fatty acid ester or of a fatty alcohol chosen from:
   2-ethylhexyl 2-ethylhexanoate
   isopropyl myristate
   diethylene glycol monoethyl ether myristate
   isopropyl palmitate
   2-octyldodecanol
   2-ethylhexyl undecylenate
   2-ethylhexyl succinate
   2-ethylhexyl 12-hydroxystearate
   2-ethylhexyl 12-acetoxystearate
   glyceryl isostearate
   hexyl laurate
4) from 44% to 84.9% of a physiologically acceptable non-aqueous solvent capable of dissolving the release matrix, the active principle and the transcutaneous absorption promoter as well as of being eliminated rapidly by evaporation on contact with the skin, in particular ethanol or isopropanol.

The compositions according to the invention for transdermal administration may be prepared, in a conventional manner, by mixing together the various constituents in the chosen proportions.

For example, it is possible, with stirring, to dissolve the transcutaneous absorption promoter in the physiological solvent and then to add the active principle and, lastly, the release matrix.

All of the substances entering into the compositions of the invention constitute known products or products which may be prepared by known methods, some of these products being commercially available.

The transdermal compositions of the invention thus obtained may be applied by any means to a predetermined area of skin, for example to an area of between 10 and 40 cm$^2$, for example 30 cm$^2$, in particular and preferably by direct spraying using a doser pump of a type which is known and marketed without the aid of a propellant such as a compressed or liquefied gas.

Although the state of the art asserts the opposite, it has been observed, surprisingly, that a release matrix formed of ethylcellulose does not cause any obstruction by sticking at the outlet of the spray head endpiece, such that the compositions of the invention may be sprayed without the need of a propellant gas and without fear of deterioration of the spray container.

If so desired, the compositions of the invention may, however, be administered by spraying from a container fitted with a dose valve, additionally containing a compressed propellant gas such as nitrogen or nitrous oxide, or a liquefied gas such as butane.

According to another subject, the invention relates to a matrix intended for pharmaceutical compositions for transdermal administration comprising:

a) a polymeric matrix, for the release of an active principle, capable of forming a flexible film after drying
b) a promoter of transcutaneous absorption of an active principle
c) a physiologically acceptable non-aqueous solvent capable of dissolving the release matrix and the transcutaneous absorption promoter and also capable of being rapidly removed by evaporation on contact with the skin.

The polymeric matrix will be selected from polymeric or copolymeric substances, in particular from cellulose polymers or copolymers as detailed above, whereas the transcutaneous absorption promoter will feature among aliphatic fatty acid esters or aliphatic fatty alcohols as described above, in particular esters of formula I or alcohols of formula II.

As regards the physiologically acceptable non-aqueous solvent, this is a compound with a boiling point below 100° C. at atmospheric pressure, as mentioned above.

These various components of the matrix for the transdermal pharmaceutical composition will be distributed such that, within the pharmaceutical composition in question containing the active principle, the release matrix represents from 0% to 6%, the transcutaneous absorption promoter represents from 15% to 30% and the physiologically acceptable non-aqueous solvent represents from 44% to 84.9%, these percentages being expressed by weight of the final pharmaceutical composition.

These matrices for transdermal compositions according to the invention may be prepared, in a conventional manner, by mixing together, in the chosen proportions, the various ingredients constituting them.

The film-forming compositions of the invention and the matrices for transdermal compositions according to the invention have incontrovertible advantages since they are capable of bringing about the transcutaneous diffusion of an active principle, for example oestradiol, so as to produce constant and controlled plasma levels over a prolonged period of at least 12 hours from a covered area of skin of about 10 to 40 cm$^2$.

The blood levels of active principle thus supplied are compatible with a therapeutic treatment, in contrast with the levels released by the compositions and matrices for known transdermal compositions such as those described, for example, in patent EP 0,319,555.

Moreover, while being free of any unpleasant odour, the compositions and matrices for transdermal compositions according to the invention spread into a uniform film over the selected area of skin and, to this end, do not necessarily require intermediate propellant gases, which are harmful to the environment.

These films are sufficiently flexible and resistant to abrasion to avoid any deterioration on the skin of a patient and are tolerated better than the known transdermal devices since, on account of their thinness and the absence of any covering, the gaseous and aqueous exchanges with the exterior are not necessarily disrupted.

Lastly, the compositions of the invention, in the form of flexible films, provide a more comfortable feel for the patient than a transdermal patch and, on account of their transparency, are entirely invisible.

Various tests were carried out, both in vitro and in vivo so as to demonstrate the characteristics and particular features of the compositions of the invention.

I. In Vitro Tests

A. Matrix: 5% Ethylcellulose

Active Principle: Oestradiol

The transcutaneous passage of an active principle incorporated into an absorption promoter vehicle may be estimated quantitatively by measuring the flow of this active principle liable to cross the skin.

The tests, involving compositions of the invention, were performed in vitro in diffusion cells of Frantz type, which make it possible to obtain very reproducible experimental conditions, facilitating the comparative studies.

These diffusion cells, which possess a receiver compartment with a volume of 30 ml, are desired especially with the aim of being able to test formulations of "spray" type to be sprayed onto a 10 cm² area of skin.

In the test performed, according to the method recommended in Curr. Probl. Dermatol. 7, 58–68 (1978), a study was thus made of the percutaneous absorption of oestradiol crossing biopsies of 10 cm² of shaven rat dorsal skin placed on the diffusion cells in question.

To this end, 50 μl of a composition of the invention containing oestradiol were applied by spraying and this active principle in the receiver liquid in contact with the dermal face of the skin was assayed after 8, 24 and 30 hours.

Since the permeability of the skin to passage of the active principle was sometimes very different from one batch of animals to another, the results obtained are essentially comparative within a same series of studies.

a) Composition Containing 2% Oestradiol

|  | % by weight |
|---|---|
| Ethylcellulose | 5% |
| Oestradiol | 2% |
| Transcutaneous absorption promoter | 20% |
| Ethanol | 73% |

In a first series of tests, carried out with Compounds 1, 2, 5, 6, 8, 9 and 11, oestradiol flows ranging from 0.115 to 0.330 μg h⁻¹ cm⁻² were recorded, in a second series with Compounds 1, 2, 7 and 10, flows ranging from 0.121 to 0.290 μg h⁻¹ cm⁻² were recorded and, in a third series with Compounds 1, 3 and 4, flows of between 0.159 to 0.280 μg h⁻¹ cm⁻² were recorded.

These results show that the flows generated by Compounds 2 to 11 are comparable with those recorded with Compound 1, without any genuinely significant difference having been recorded.

An additional series of tests was performed with a composition of the invention of the following formulation:

|  | % by weight |
|---|---|
| Ethylcellulose | 5% |
| Oestradiol | 2% |
| Compound 1 | W% |
| Ethanol | (93-W)% |

The results reported below were recorded:

| Compound 1 (W%) | Flow ($\mu$g h⁻¹ cm⁻²) |
|---|---|
| 0 | 0.198 ± 0.038 |
| 5 | 0.310 ± 0.032 |
| 10 | 0.460 ± 0.066 |
| 15 | 0.501 ± 0.122 |
| 20 | 0.603 ± 0.136 |

These results show that the diffusional flows of oestradiol increase proportionally to the concentration of the promoter within the composition.

However, beyond 20%, no further increase characteristic of the transcutaneous flows of oestradiol were recorded, these nevertheless remaining high, as proven by the results below:

| Compound 1 (W%) | Flow ($\mu$g h⁻¹ cm⁻²) |
|---|---|
| 20 | 0.369 ± 0.058 |
| 30 | 0.197 ± 0.019 |

For comparative purposes, tests were also carried out: either with a composition according to the invention comprising, by weight:

|  |  |
|---|---|
| Ethylcellulose | 5% |
| Oestradiol | 2% |
| Compound 1 | 20% |
| Ethanol | 73% | or with compositions of the state of the art represented by patent EP 0,319,555 (compositions X and Y) comprising, by weight:

|  |  |
|---|---|
| Oestradiol | 2% |
| Poly(n-butyl methacrylate) | 3.66% |
| Polyvinylpyrrolidone VA (PVP VA*) (50% ethanolic solution) | 6.66% |
| Ethanol | 11.66% |
| Sorbitan macrogollaurate | 1.66% |
| Methylene chloride | 74.36% |

PVP VA: two types of PVP VA were used, one containing 30% polyvinylpyrrolidone (PVP VA 335 ISP) in the composition X and the other containing 70% polyvinylpyrrolidone (PVP VA 735 ISP) in the composition Y.

The results obtained were as follows:

| Compositions | Flow ($\mu$g h⁻¹ cm⁻²) |
|---|---|
| Of the invention | 0.295 ± 0.105 |
| Composition X | 0.032 ± 0.01 |
| Composition Y | 0.024 ± 0.007 |

These results show the distinct superiority of the compositions of the invention over the prior art compositions, the flows recorded being 8 to 9 times larger.

An additional test, undertaken with compositions X and Y sprayed onto 10 cm² of aluminium and then placed in contact with the skin after evaporation of the solvents, according to the technique described in patent EP 0,319,555 mentioned above, revealed transcutaneous diffusional flows of oestradiol of 0.009±0.011 and 0.002±0.003 $\mu$g h$^{-1}$ cm$^{-2}$ respectively.

b) Compositions Containing 1% Oestradiol

In another series of tests, similar tests were performed for the purpose of demonstrating the superiority of the compositions of the invention over identical transdermal compositions in which the transcutaneous absorption promoter was replaced so as to estimate the qualities of the compounds of formula I.

To this end, compositions corresponding to the following formulation were used:

| | |
|---|---|
| Ethylcellulose | 5% by weight |
| Oestradiol | 1% by weight |
| Compound Z | 20% by weight |
| Ethanol | 74% by weight | compound Z being either a transcutaneous absorption promoter of formula I above or a compound derived from the state of the art.

Similarly, a comparative test was performed using a gel containing oestradiol (oestradiol: 0.06%*; 95° ethanol: 40*%; Carbopol®: 1%*; triethanolamine: 1%*; purified water: qs 100%) marketed under the brand name Oestrogel®.

% by weight
The following results were obtained:

1) Sprayable compositions

| Compound Z | Flow ($\mu$g h$^{-1}$ cm$^{-2}$) |
|---|---|
| Compound 1 | 0.116 ± 0.042 |
| Diethylene glycol mono-ethyl ether (Transcutol ®) | 0.032 ± 0.014 |
| Dimethylisosorbide | 0.028 ± 0.021 |

2) Gel

| Oestrogel ® | 0.014 ± 0.003 |
|---|---|

These results show that the transcutaneous diffusional flows of oestradiol per cm², generated by the composition of the invention containing compound 1, are by far superior to those obtained with sprayable compositions in which this compound 1 has been replaced, since they are 3 to 4 times larger.

In the case of the gel, it is observed that the transcutaneous diffusional flows of the active principle are 7 to 8 times lower than those produced by the composition of the invention.

When expressed in terms of actual application area, namely 30 cm² for the composition of the invention and 100 cm² for the product Oestrogel®, these results reflect that twice as much active principle diffuses from the composition of the invention over 24 hours when compared with the gel, since about 40 $\mu$g was recorded for the gel as opposed to 80 $\mu$g for the composition of the invention.

Moreover, experimental studies performed with film-forming compositions containing 1% oestradiol according to the invention, washed 8 hours after application, showed no incidence of diffusion of the active principle even 30 hours after applying it to the skin.

From the set of results reported above, it may be concluded that the transdermal compositions of the invention have a distinct superiority over the other compositions tested, due in particular to the presence of a promoter of transcutaneous absorption of the active principle, which is capable of contributing efficiently towards the production of sizeable transdermal diffusional flows of this active principle.

These sizeable transdermal flows lead one to expect better performance of the compositions of the invention, for example in order to generate, from the same application area of skin, plasma levels of medicinal principle which are better suited to therapy.

c) Compositions Containing 2%, 4% or 6% Oestradiol

Tests similar to that described in paragraph I.A. above were performed in order to show the influence of the oestradiol concentration on the transcutaneous flows.

To this end, compositions corresponding to the following formulation were used:

| | % by weight |
|---|---|
| Ethylcellulose | 5% |
| Oestradiol | Oes% |
| Compound 1 | 20% |
| Solvent | (75-Oes)% |

The following results were obtained:

| Oestradiol (Oes%) | Solvent: (75-Oes)% | Flow ($\mu$g h$^{-1}$ cm$^{-2}$) |
|---|---|---|
| 2 | Ethanol: 73% | 0.369 ± 0.058 |
| 4 | Ethanol/isopropanol 30/70: 71% | 0.509 ± 0.050 |
| 6 | Isopropanol: 69% | 0.769 ± 0.159 |

B. Matrix: 0%, 2%, 3%, 4%, 5% or 6% Ethylcellulose
Active Principle: Oestradiol

Tests similar to that described in paragraph I.A. were performed in vitro in diffusion cells of Frantz type, using a composition of the invention of the following formulation:

| | % by weight |
|---|---|
| Ethylcellulose | Et% |
| Oestradiol | 2% |
| Compound 1 | 20% |
| Ethanol | (78-Et)% |

The results reported below were recorded:

| Ethylcellulose (Et%) | Flow ($\mu$g h$^{-1}$ cm$^{-2}$) |
|---|---|
| 0 | 0.214 ± 0.032 |
| 2 | 0.362 ± 0.079 |
| 3 | 0.445 ± 0.099 |
| 4 | 0.354 ± 0.092 |
| 5 | 0.347 ± 0.095 |
| 6 | 0.397 ± 0.034 |

These results show that the ethylcellulose concentration has only a slight influence on the oestradiol flows at equilibrium.

C. Matrix : 5% Ethylcellulose

Active Principles: oestradiol, selegiline, ibuprofen, clonidine, testosterone, norethindrone acetate, acetylsalicylic acid.

To this end, an in vitro test was used in diffusion cells of Frantz type similar to that described above for oestradiol (paragraph I.A. above).

All of the quantitative studies performed related to radio-labelled active principles.

To this end, 50 μl of a composition containing 10 μCi of radiolabelled active principle were applied by spraying onto 10 cm$^2$ of skin and the total radioactivity in 1 ml samples of receiver liquid was assayed after 7, 24 and 30 hours by liquid scintillation in the presence of a scintillation cocktail.

The tests with various active principles were performed comparative to compositions containing 17β-oestradiol radiolabelled with tritium by isotopic dilution (2,4,6,7-$^3$H-oestradiol)

a) Active Principle: Seleqiline

The tests, performed on the molecule labelled with tritium by isotopic dilution, gave the following results:

|  | % by weight | Flow (μg h$^{-1}$ cm$^{-2}$) |
|---|---|---|
| 1st series of tests |  |  |
| Ethylcellulose | 5 |  |
| Oestradiol | 2 | 0.732 ± 0.110 |
| Compound 1 | 20 |  |
| Ethanol | 73 |  |
| Ethylcellulose | 5 |  |
| Selegiline | 4 | 4.010 ± 0.898 |
| Compound 7 | 20 |  |
| Ethanol | 71 |  |
| 2nd series of tests |  |  |
| Ethylcellulose | 5 |  |
| Oestradiol | 2 | 0.598 ± 0.173 |
| Compound 1 | 20 |  |
| Ethanol | 73 |  |
| Ethylcellulose | 5 |  |
| Selegiline | 10 | 7.878 ± 2.600 |
| Compound 1 | 20 |  |
| Ethanol | 65 |  |
| Ethylcellulose | 5 |  |
| Selegiline | 10 | 6.645 ± 0.809 |
| Compound 2 | 20 |  |
| Ethanol | 65 |  | b) Active Principle: Ibuprofen

The tests, carried out on the molecule radio-labelled with tritium by isotopic dilution, gave the following results:

|  | % by weight | Flow (μg h$^{-1}$ cm$^{-2}$) |
|---|---|---|
| 1st series of tests |  |  |
| Ethylcellulose | 5 |  |
| Oestradiol | 2 | 0.909 ± 0.184 |
| Compound 1 | 20 |  |
| Ethanol | 73 |  |
| Ethylcellulose | 5 |  |
| Ibuprofen | 2 | 1.432 ± 0.307 |
| Compound 1 | 20 |  |
| Ethanol | 73 |  |

An additional comparative test carried out with a composition containing 5% ethylcellulose, 2% ibuprofen and 93% ethanol gave transcutaneous diffusional flows of 0.780 μg h$^{-1}$ cm$^{-2}$.

This result clearly shows that compound 1 acts as a transdermal absorption promoter for ibuprofen.

|  | % by weight | Flow (μg h$^{-1}$ cm$^{-2}$) |
|---|---|---|
| 2nd series of tests |  |  |
| Ethylcellulose | 5 |  |
| Oestradiol | 2 | 0.805 ± 0.102 |
| Compound 1 | 20 |  |
| Ethanol | 73 |  |
| Ethylcellulose | 5 |  |
| Ibuprofen | 2.5 | 1.911 ± 0.137 |
| Compound 1 | 20 |  |
| Ethanol | 72.5 |  |
| Ethylcellulose | 5 |  |
| Ibuprofen | 2 | 1.272 ± 0.292 |
| Compound 7 | 20 |  |
| Ethanol | 73 |  | c) Active Principle: Clonidine

The tests, performed with the molecule labelled with tritium by isotopic dilution (4-phenyl-$^3$H-clonidine hydrochloride), gave the following results:

|  | % by weight | Flow (μg h$^{-1}$ cm$^{-2}$) |
|---|---|---|
| Ethylcellulose | 5 | 0.761 ± 0.134 |
| Oestradiol | 2 |  |
| Compound 1 | 20 |  |
| Ethanol | 73 |  |
| Ethylcellulose | 5 | 0.213 ± 0.127 |
| Clonidine | 2 |  |
| Compound 1 | 20 |  |
| Ethanol | 73 |  |

An additional comparative test carried out with a composition containing 5% ethylcellulose, 2% clonidine and 93% ethanol gave transcutaneous diffusional flows of 0.079±0.118 μg h$^1$ cm$^2$.

This result shows that compound 1 acts as a transdermal absorption promoter for clonidine.

d) Active Principle: Testosterone

The tests, performed on the molecule labelled with tritium by isotopic dilution (1,2,6,7-$^3$H-testosterone), gave the following results:

|  | % by weight | Flow (μg h$^{-1}$ cm$^{-2}$) |
|---|---|---|
| 1st series of tests |  |  |
| Ethylcellulose | 5 | 0.679 ± 0.065 |
| Oestradiol | 2 |  |
| Coxnpound 1 | 20 |  |
| Ethanol | 73 |  |
| Ethylcellulose | 5 | 1.637 ± 0.164 |
| Testosterone | 2 |  |
| Compound 1 | 20 |  |
| Ethanol | 73 |  |
| Ethylcellulose | 5 | 1.274 ± 0.128 |
| Testosterone | 2 |  |
| Compound 1 | 15 |  |
| Ethanol | 78 |  |
| 2nd series of tests |  |  |
| Ethylcellulose | 5 | 1.419 ± 0.189 |
| Testosterone | 2 |  |
| Compound 1 | 20 |  |
| Ethanol | 73 |  |

An additional test carried out with a composition containing 5% ethylcellulose, 2% testosterone and 93% ethanol gave transcutaneous diffusional flows of 0.443±0.190 μg h$^1$ cm$^2$.

This result shows that compound 1 does indeed act as a transdermal absorption promoter for testosterone.

e) Active Principle: Norethindrone Acetate

The tests, performed with the molecule labelled with tritium by isotopic dilution, gave the following results:

|  | % by weight | Flow ($\mu g\ h^{-1}\ cm^{-2}$) |
|---|---|---|
| 1st series of tests | | |
| Ethylcellulose | 5 | 0.588 ± 0.077 |
| Oestradiol | 2 | |
| Compound 1 | 20 | |
| Ethanol | 73 | |
| Ethylcellulose | 5 | 0.438 ± 0.194 |
| Norethindrone acetate | 3 | |
| Compound 1 | 20 | |
| Ethanol | 72 | |
| Ethylcellulose | 5 | 0.241 ± 0.101 |
| Norethindrone acetate | 2 | |
| Compound 7 | 20 | |
| Ethanol | 73 | |
| 2nd series of tests | | |
| Ethylcellulose | 5 | 0.276 ± 0.143 |
| Oestradiol | 2 | |
| Compound 1 | 20 | |
| Ethanol | 73 | |
| Ethylcellulose | 5 | 0.341 ± 0.078 |
| Norethindrone acetate | 2 | |
| Compound 1 | 20 | |
| Ethanol | 73 | |

An additional test carried out with a composition containing 5% ethylcellulose, 2% norethindrone acetate and 93% ethanol gave transcutaneous diffusional flows of 0.066±0.026 $\mu g\ h^{-1}\ cm^{-2}$, which shows that compound 1 does indeed act as a transdermal absorption promoter for norethindrone acetate.

f) Active Principle: Acetylsalicylic Acid

The tests, performed with the molecule labelled with $^{14}C$ by isotopic dilution ($^{14}C$-carboxyl acetylsalicylic acid), gave the following results:

|  | % by weight | Flow ($\mu g\ h^{-1}\ cm^{-2}$) |
|---|---|---|
| Ethylcellulose | 5 | 0.554 ± 0.108 |
| Oestradiol | 2 | |
| Compound 1 | 20 | |
| Ethanol | 73 | |
| Ethylcellulose | 5 | 1.724 ± 0.153 |
| Acetylsalicylic acid | 2 | |
| Compound 1 | 20 | |
| Ethanol | 73 | |
| Ethylcellulose | 5 | 1.689 ± 0.127 |
| Acetylsalicylic acid | 2 | |
| Compound 7 | 20 | |
| Ethanol | 73 | |

D. Matrix: Polyvinylpyrrolidone/vinyl Acetate

Active Principle: Oestradiol

An additional series of tests similar to that described in paragraph I.A. was performed so as to determine the transcutaneous diffusional flows of oestradiol from compositions of the invention containing a polyvinylpyrrolidone/vinyl acetate (PVP VA) matrix.

To this end, compositions of the following formulation were used:

|  | % by weight |
|---|---|
| PVP VA | P % |
| Oestradiol | 2% |
| Compound 1 | 20% |
| Ethanol | (78-P)% | compared with a composition C of the invention containing a matrix formed of ethylcellulose:

|  | % by weight |
|---|---|
| Ethylcellulose | 5% |
| Oestradiol | 2% |
| Compound 1 | 20% |
| Ethanol | 73% |

The following results were obtained:

| PVP VA (P%) | Flow ($\mu g\ h^{-1}\ cm^{-2}$) |
|---|---|
| 2 | 0.165 ± 0.014 |
| 3 | 0.212 ± 0.026 |
| 4 | 0.209 ± 0.023 |
| 5 | 0.205 ± 0.037 |
| Composition C | 0.321 ± 0.073 |

For the purposes of a comparative test, an attempt was made to prepare a transdermal composition containing 2% oestradiol, a matrix, a solvent and a propellant gas similar to those described in patent EP 0,319,555, namely 2.5% PVP VA, 2.5% n-butyl methacrylate, 15% ethanol, 13% dichloromethane and 61.5% freon to which was added 5% of compound 1, the promoter used in the present invention.

However, this composition containing 2% oestradiol could not be prepared, since this active principle did not manage to dissolve in such a mixture.

Lastly, a composition of the following formulation:

|  | % by weight |
|---|---|
| PVP VA | 3% |
| Oestradiol | 2% |
| Compound 1 | 25% |
| Ethanol | 70% | gave transcutaneous diffusional flows of 0.232±0.028 $\mu g\ h^{-1}\ cm^{-2}$.

II. In Vivo Tests

Tests were also carried out in vivo on Yucatan type micropigs weighing about 13 kg, onto which were applied:
either 100 $\mu l$ of a composition containing 2% oestradiol according to the invention, by spraying into 30 $cm^2$ of skin, this being equivalent to 1.5 mg of oestradiol
or 2.5 g of Oestrogel® gel by spreading onto 100 $cm^2$ of skin, this also being equivalent to 1.5 mg of oestradiol.

The levels of oestradiol in the plasma were then determined at various time intervals.

Under these conditions of application, comparable to those which may be used by women, the plasma concentrations of oestradiol produced by the composition of the invention and by the Oestrogel® gel were respectively about 390 pg/ml and 170 pg/ml 8 hours after application, and about 304 pg/ml and 160 pg/ml 24 hours after application.

The composition of the invention consequently has a performance level which is twice as high as the Oestrogel® gel for the production of oestradiol levels in the blood over a period of 24 hours.

Similar comparative tests, performed with compositions X and Y according to the state of the art, also demonstrated a significant superiority of the compositions of the invention for the production of sizeable and prolonged levels of oestradiol in the blood.

The following non-limiting examples illustrate the preparation of compositions of the invention as well as matrices for transdermal compositions according to the invention.

EXAMPLE 1

Transdermal Composition Containing Oestradiol 100 g of a transdermal composition of the following formulation is prepared:

|  | % by weight |
|---|---|
| Ethylcellulose 6 mPa sec | 5% |
| Oestradiol | 2% |
| 2-Ethylhexyl 2-ethylhexanoate | 20% |
| Ethanol | 73% | by mixing together, for 30 seconds and with magnetic stirring, 73 g of ethanol and 20 g of 2-ethylhexyl 2-ethylhexanoate.

2 g of oestradiol were then added portionwise to the mixture obtained and, after complete dilution (5 minutes), 5 g of ethylcellulose 6 mPa sec were introduced with vigorous stirring, so as to prevent the formation of lumps. The final solution obtained is homogeneous and slightly opalescent.

For the purposes of administration by spraying, aluminium cans are filled with 5 ml of the solution obtained above and are equipped with a crimping vasopump containing a press-button.

The pump is actuated twice in order to prime it before its first use.

EXAMPLES 2 to 38

Transdermal Compositions Containing Oestradiol

The following formulations of transdermal compositions were prepared using the same process as in Example 1:

|  |  | % by weight |
|---|---|---|
| EX. 2 | Ethylcellulose | 5% |
|  | Oestradiol | 1% |
|  | 2-Ethylhexyl 2-ethylhexanoate | 20% |
|  | Ethanol | 74% |
| EX. 3 | Ethylcellulose | 5% |
|  | Oestradiol | 2% |
|  | 2-Ethylhexyl 12-acetoxystearate | 20% |
|  | Ethanol | 73% |
| EX. 4 | Ethylcellulose | 5% |
|  | Oestradiol | 1.5% |
|  | Hexyllaurate | 20% |
|  | Ethanol | 73.5% |
| EX. 5 | Ethylcellulose | 5% |
|  | Oestradiol | 2.5% |
|  | 2-Octyldodecanol | 20% |
|  | Ethanol | 72.5% |
| EX. 6 | Ethylcellulose | 5% |
|  | Oestradiol | 3% |
|  | 2-Ethylhexyl 12-hydroxystearate | 20% |
|  | Ethanol | 72% |
|  | 2-Ethylhexyl 12-hydroxystearate | 20% |
|  | Ethanol | 72% |

-continued

|  |  | % by weight |
|---|---|---|
| EX. 7 | Ethylcellulose | 2% |
|  | Oestradiol | 1% |
|  | 2-Ethylhexyl 2-ethylhexanoate | 20% |
|  | Ethanol | 77% |
| EX. 8 | Ethylcellulose | 5% |
|  | Testosterone | 2% |
|  | 2-Ethylhexyl 2-ethylhexanoate | 20% |
|  | Ethanol | 73% |
| EX. 9 | Ethylcellulose | 5% |
|  | Oestradiol | 2% |
|  | 2-Ethylhexyl 2-ethylhexanoate | 5% |
|  | Ethanol | 88% |
| EX. 10 | Ethylcellulose | 5% |
|  | Oestradiol | 2% |
|  | 2-Ethylhexyl 2-ethylhexanoate | 15% |
|  | Ethanol | 78% |
| EX. 11 | Ethylcellulose | 5% |
|  | Oestradiol | 2% |
|  | 2-Ethylhexyl 2-ethylhexanoate | 20% |
|  | Isopropanol | 73% |
| EX. 12 | Ethylcellulose | 5% |
|  | Oestradiol | 4% |
|  | 2-Ethylhexyl 2-ethylhexanoate | 20% |
|  | Ethanol/isopropanol 30/70 | 71% |
| EX. 13 | Ethylcellulose | 5% |
|  | Oestradiol | 6% |
|  | 2-Ethylhexyl 2-ethylhexanoate | 20% |
|  | Isopropanol | 69% |
| EX. 14 | Oestradiol | 2% |
|  | 2-Ethylhexyl 2-ethylhexanoate | 20% |
|  | Ethanol | 78% |
| EX. 15 | Ethylcellulose | 2% |
|  | Oestradiol | 2% |
|  | 2-Ethylhexyl 2-ethylhexanoate | 20% |
|  | Ethanol | 76% |
| EX. 16 | Ethylcellulose | 3% |
|  | Oestradiol | 2% |
|  | 2-Ethylhexyl-2-ethylhexanoate | 20% |
|  | Ethanol | 75% |
| EX. 17 | Ethylcellulose | 4% |
|  | Oestradiol | 2% |
|  | 2-Ethylhexyl 2-ethylhexanoate | 20% |
|  | Ethanol | 74% |
| EX. 18 | Ethylcellulose | 6% |
|  | Oestradiol | 2% |
|  | 2-Ethylhexyl 2-ethylhexanoate | 20% |
|  | Ethanol | 72% |
| EX. 19 | Ethylcellulose | 5% |
|  | Selegiline | 10% |
|  | 2-Ethylhexyl 2-ethylhexanoate | 20% |
|  | Ethanol | 65% |
| EX. 20 | Ethylcellulose | 5% |
|  | Selegiline | 4% |
|  | 2-Ethylhexyl succinate | 20% |
|  | Ethanol | 71% |
| EX. 21 | Ethylcellulose | 5% |
|  | Selegiline | 10% |
|  | Isopropyl myristate | 20% |
|  | Ethanol | 65% |
| EX. 22 | Ethylcellulose | 5% |
|  | Ibuprofen | 2% |
|  | 2-Ethylhexyl 2-ethylhexanoate | 20% |
|  | Ethanol | 73% |
| EX. 23 | Ethylcellulose | 5% |
|  | Ibuprofen | 2.5% |
|  | 2-Ethylhexyl 2-ethylhexanoate | 20% |
|  | Ethanol | 72.5% |
| EX. 24 | Ethylcellulose | 5% |
|  | Ibuprofen | 2% |
|  | 2-Ethylhexyl succinate | 20% |
|  | Ethanol | 73% |
| EX. 25 | Ethylcellulose | 5% |
|  | Clonidine | 2% |
|  | 2-Ethylhexyl 2-ethylhexanoate | 20% |
|  | Ethanol | 73% |

-continued

|  |  | % by weight |
|---|---|---|
| EX. 26 | Ethylcellulose | 5% |
|  | Testosterone | 2% |
|  | 2-Ethylhexyl 2-ethylhexanoate | 15% |
|  | Ethanol | 78% |
| EX. 27 | Ethylcellulose | 5% |
|  | Norethindrone acetate | 3% |
|  | 2-Ethylhexyl 2-ethylhexanoate | 20% |
|  | Ethanol | 72% |
| EX. 28 | Ethylcellulose | 5% |
|  | Norethindrone acetate | 2% |
|  | 2-Ethylhexyl succinate | 20% |
|  | Ethanol | 73% |
| EX. 29 | Ethylcellulose | 5% |
|  | Norethindrone acetate | 2% |
|  | 2-Ethylhexyl 2-ethylhexanoate | 20% |
|  | Ethanol | 73% |
| EX. 30 | Ethylcellulose | 5% |
|  | Acetylsalicylic acid | 2% |
|  | 2-Ethylhexyl 2-ethylhexanoate | 20% |
|  | Ethanol | 73% |
| EX. 31 | Ethylcellulose | 5% |
|  | Acetylsalicylic acid | 2% |
|  | 2-Ethylhexyl succinate | 20% |
|  | Ethanol | 73% |
| EX. 32 | PVP VA | 2% |
|  | Oestradiol | 2% |
|  | 2-Ethylhexyl 2-ethylhexanoate | 20% |
|  | Ethanol | 76% |
| EX. 33 | PVP VA | 3% |
|  | Oestradiol | 2% |
|  | 2-Ethylhexyl 2-ethylhexanoate | 20% |
|  | Ethanol | 75% |
| EX. 34 | PVP VA | 4% |
|  | Oestradiol | 2% |
|  | 2-Ethylhexyl 2-ethylhexanoate | 20% |
|  | Ethanol | 74% |
| EX. 35 | PVP VA | 5% |
|  | Oestradiol | 2% |
|  | 2-Ethylhexyl 2-ethylhexanoate | 20% |
|  | Ethanol | 73% |
| EX. 36 | PVP VA | 3% |
|  | Oestradiol | 2% |
|  | 2-Ethylhexyl 2-ethylhexanoate | 25% |
|  | Ethanol | 70% |
| EX. 37 | Ethylcellulose | 5% |
|  | Oestradiol | 2% |
|  | 2-Ethylhexyl 2-ethylhexanoate | 30% |
|  | Ethanol | 63% |

EXAMPLE 38

Matrix For a Transdermal Composition 98 g of a matrix for a transdermal composition were prepared by mixing together, for 30 seconds, 73 g of ethanol and 20 g of 2-ethylhexyl 2-ethylhexanoate. 5 g of ethylcellulose 6 mPa sec are then added, with vigorous stirring, so as to prevent the formation of lumps.

The matrix thus obtained is ready to receive an active principle by incorporation, so as to form a pharmaceutical composition containing 2% by weight of this active principle, which may be applied by spraying.

We claim:

1. Pharmaceutical composition for transdermal administration, comprising:
   a) optionally, a polymeric release matrix capable of forming a flexible film after drying, selected from the group consisting of cellulose polymers and cellulose copolymers,
   b) an active principle
   c) 15 to 30% of the weight of the composition of a promoter of transcutaneous absorption of the active principle
   d) 44 to 84.9% of the weight of the composition of a physiologically acceptable non-aqueous solvent appropriate to dissolve the active principle, the transcutaneous absorption promoter and, if present, the release matrix and be rapidly removed by evaporation on contact with the skin, the transcutaneous absorption promoter being selected from the group consisting of:

an aliphatic fatty acid ester which is soluble in the physiologically acceptable non-aqueous solvent and is of general formula:

$$R-\overset{O}{\underset{\|}{C}}-OR_1 \qquad \text{I}$$

in which R is selected from the group consisting of a linear or branched $C_2$–$C_{17}$ alkyl or alkenyl group and a linear or branched $C_2$–$C_{17}$ alkyl or alkenyl group substituted with a radical selected from the group consisting of hydroxyl, carboxy and $C_1$–$C_4$ acyloxy group and $R_1$ is selected from the group consisting of a linear or branched $C_3$–$C_8$ alkyl group and a linear or branched $C_3$–$C_8$ alkyl group substituted with one or two hydroxyl groups, or $R_1$ represents a group $-CH_2-CH_2-O-(CH_2)_2-O-CH_2-CH_3$, the aliphatic fatty acid ester containing a minimum of 10 carbon atoms and a maximum of 2 hydroxyl groups an aliphatic fatty alcohol which is soluble in the physiologically acceptable non-aqueous solvent and is of general formula:

$$R_2-OH \qquad \text{II}$$

in which $R_2$ represents a $C_{10}$–$C_{20}$ alkyl group.

2. Pharmaceutical composition according to claim 1, wherein the polymeric release matrix is present in a proportion of from 0% to 6% of the weight of the composition.

3. Pharmaceutical composition according to claim 2, wherein the polymeric release matrix is present in a proportion of from 1% to 5% of the weight of the composition.

4. Pharmaceutical composition according to claim 1, wherein the active principle is present in a proportion of from 0.1% to 20% of the weight of the composition.

5. Pharmaceutical composition according to claim 1, wherein the transcutaneous absorption promoter is present in a proportion of from 15% to 25% of the weight of the composition.

6. Pharmaceutical composition according to claim 1, wherein the polymeric release matrix is a cellulose polymer or copolymer which is soluble in the physiologically acceptable non-aqueous solvent.

7. Pharmaceutical composition according to claim 6, wherein the cellulose polymer or copolymer is selected from the group consisting of ethylcellulose, cellulose acetate butyrate, cellulose acetate propionate, a grafted hydroxypropylmethylcellulose and an ungrafted hydroxypropylmethylcellulose.

8. Pharmaceutical composition according to claim 6, wherein the cellulose polymer or copolymer is ethylcellulose.

9. Pharmaceutical composition according to claim 1, wherein the active principle is a substance which is soluble in the physiologically acceptable non-aqueous solvent, selected from the group consisting of:
   bronchodilators; diuretics; antibacterial agents; antiacne agents; sedatives or tranquillizers; psychostimulants; anxiolytic agents; hormones; androgenic steroids;

oestrogenic steroids; progestative steroids; thyroid hormones; antipyretic agents; narcotic analgesics or major analgesics; hypoglycaemiants; antispasmodic agents; antitabagic agents; antimalaria agents; beta-blockers; antiarthritic agents; non-steroidal anti-inflammatpry agents; anti-osteoporotic agents; skin bleaching agents; vasodilators; anti-hypertensive agents; antiparkinsonian agents; anti-migraine agents; contraceptive agents; antiulcer agents; anticancer agents and nutritional supplies.

10. Pharmaceutical composition according to claim 1, wherein the active principle is selected from the group consisting of oestradiol, selegiline, ibuprofen, clonidine, norethindrone acetate, testosterone and acetylsalicylic acid.

11. Pharmaceutical composition according to claim 10, wherein the oestradiol is present in a proportion of from 0.5% to 6% of the weight of the composition.

12. Pharmaceutical composition according to claim 11, wherein the oestradiol is present in a proportion of from 1% to 2% of the weight of the composition.

13. Pharmaceutical composition according to claim 1, which contains a combination of active principles consisting of a progestative steroid and an oestrogenic steroid.

14. Pharmaceutical composition according to claim 1, wherein $R_1$ is selected from the group consisting of a isopropyl, a 2-ethylhexyl and a 1,2-dihydroxyethyl group.

15. Pharmaceutical composition according to claim 1, wherein the transcutaneous absorption promoter is selected from the group consisting of:
   2-ethylhexyl-2-ethylhexanoate
   isopropyl myristate
   diethylene glycol monoethyl ether myristate
   isopropyl palmitate
   2-octyldodecanol
   2-ethylhexyl undecylenate
   2-ethylhexyl succinate
   2-ethylhexyl 12-hydroxystearate
   2-ethylhexyl 12-acetoxystearate
   glyceryl isostearate, and
   hexyl laurate.

16. Pharmaceutical composition according to claim 1, wherein the transcutaneous absorption promoter is 2-ethylhexyl 2-ethylhexanoate.

17. Pharmaceutical composition according to claim 1, wherein the physiologically acceptable non-aqueous solvent is a compound with a boiling point below 100° C. at atmospheric pressure.

18. Pharmaceutical composition according to claim 17, wherein the compound with a boiling point below 100° C. is selected from the group consisting of dichloromethane, ethanol, isopropanol and ethyl acetate.

19. Pharmaceutical composition according to claim 17, wherein the physiologically acceptable non-aqueous solvent is ethanol.

20. Pharmaceutical composition according to claim 1, wherein:
   the cellulose polymer or copolymer is ethylcellulose
   the active principle is oestradiol
   the transcutaneous absorption promoter is 2-ethylhexyl 2-ethylhexanoate
   the physiologically acceptable solvent is ethanol.

21. Pharmaceutical composition according to claim 20, comprising:
   3% of ethylcellulose
   2% of oestradiol
   20% of 2-ethylhexyl 2-ethylhexanoate, and
   75% of ethanol.

22. Pharmaceutical composition according to claim 1, comprising:
   5% of ethylcellulose
   2% of oestradiol
   20% of 2-ethylhexyl 2-ethylhexanoate, and
   73% of ethanol.

23. Pharmaceutical composition according to claim 1, comprising:
   5% of ethylcellulose
   1% of oestradiol
   20% of 2-ethylhexyl 2-ethylhexanoate, and
   74% of ethanol.

24. Pharmaceutical composition according to claim 1, comprising:
   2% of ethylcellulose
   1% of oestradiol
   20% of 2-ethylhexyl 2-ethylhexanoate, and
   77% of ethanol.

25. Composition according to claim 1, which is applied by direct spraying without the aid of a compressed or liquefied propellant gas.

26. Composition according to claim 1, which is applied to a 10 to 40 cm² area of skin.

27. Matrix for a pharmaceutical composition intended for transdermal administration, comprising:
   a) a polymeric matrix, for the release of an active principle, capable of forming a flexible film after drying, selected from the group consisting of cellulose polymers and cellulose copolymers
   b) 15 to 30% of the weight of the composition of a promoter of transcutaneous absorption of the active principle
   c) 44 to 84.9% of the weight of the composition of a physiologically acceptable non-aqueous solvent appropriate to dissolve the active principles, the transcutaneous absorption promoter and, if present, the release matrix and be rapidly removed by evaporation on contact with the skin,
   the transcutaneous absorption promoter being selected from the group consisting of:
   an aliphatic fatty acid ester which is soluble in the physiologically acceptable non-aqueous solvent and is of general formula:

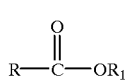

I in which R is selected from the group consisting of a linear or branched $C_2$–$C_{17}$ alkyl or alkenyl group and a linear or branched $C_2$–$C_{17}$ alkyl or alkenyl group substituted with a radical selected from the group consisting of hydroxyl, carboxy and $C_1$–$C_4$ acyloxy group and $R_1$ is selected from the group consisting of a linear or branched $C_3$–$C_8$ alkyl group and a linear or branched $C_3$–$C_8$ alkyl group substituted with one or two hydroxyl groups, or $R_1$ represents a group —$CH_2$—$CH_2$—O—$(CH_2)_2$—O—$CH_2$—$CH_3$, the aliphatic fatty acid ester containing a minimum of 10 carbon atoms and a maximum of 2 hydroxyl groups an aliphatic fatty alcohol which is soluble in the physiologically acceptable non-aqueous solvent and is of general formula:

$$R_2\text{—OH} \qquad \text{II}$$

in which $R_2$ represents a $C_{10}$–$C_{20}$ alkyl group.

28. Matrix for a pharmaceutical composition according to claim 27, wherein the cellulose polymer or copolymer is selected from the group consisting of ethylcellulose, cellulose acetate butyrate, cellulose acetate propionate, a grafted hydroxypropylmethylcellulose and an ungrafted hydroxypropylmethylcellulose.

29. Matrix for a pharmaceutical composition according to claim 28, wherein the cellulose polymer or copolymer is ethylcellulose.

30. Matrix for a pharmaceutical composition according to claim 27, wherein the transcutaneous absorption promoter is selected from the group consisting of:

2-ethylhexyl-2-ethylhexanoate isopropyl myristate diethylene glycol monoethyl ether myristate isopropyl palmitate 2-octyidodecanol 2-ethylhexyl undecylenate 2-ethylhexyl succinate 2-ethylhexyl 12-hydroxystearate 2-ethylhexyl 12-acetoxystearate glyceryl isostearate, and hexyl laurate.

31. Matrix for a pharmaceutical composition according to claim 30, wherein the transcutaneous absorption promoter is 2-ethylhexyl 2-ethylhexanoate.

32. Matrix for a pharmaceutical composition according to claim 27, wherein the physiologically acceptable non-aqueous solvent is a compound with a boiling point below 100° C. at atmospheric pressure.

33. Matrix for a pharmaceutical composition according to claim 32, wherein the compound with a boiling point below 100° C. is selected from the group consisting of dichloromethane, ethanol, isopropanol and ethyl acetate.

34. Matrix for a transdermal composition according to claim 32, wherein the compound with a boiling point below 100° C. is ethanol.

35. Matrix for a pharmaceutical composition according to claim 27, wherein within the said pharmaceutical composition containing the active principle, the release matrix represents from 0% to 6%, the transcutaneous absorption promoter represents from 15% to 30% and the physiologically acceptable non-aqueous solvent represents from 44% to 84.9%, these percentages being expressed by weight of the final pharmaceutical composition.

* * * * *